US012260308B2

(12) United States Patent
Smith et al.

(10) Patent No.: US 12,260,308 B2
(45) Date of Patent: Mar. 25, 2025

(54) APPARATUS FOR POST ACTION PLANNING AND METHOD OF USE

(71) Applicant: Strategic Coach, Toronto (CA)

(72) Inventors: Barbara Sue Smith, Toronto (CA); Daniel J. Sullivan, Toronto (CA)

(73) Assignee: The Strategic Coach Inc., Toronto (CA)

( * ) Notice: Subject to any disclaimer, the term of this patent is extended or adjusted under 35 U.S.C. 154(b) by 0 days.

(21) Appl. No.: 18/142,411

(22) Filed: May 2, 2023

(65) Prior Publication Data

US 2024/0370763 A1    Nov. 7, 2024

(51) Int. Cl.
*G06N 20/00*    (2019.01)
*G16H 20/30*    (2018.01)
*G16H 50/30*    (2018.01)

(52) U.S. Cl.
CPC ............ *G06N 20/00* (2019.01); *G16H 20/30* (2018.01); *G16H 50/30* (2018.01)

(58) Field of Classification Search
CPC ......... G06N 20/00; G16H 20/30; G16H 50/30
See application file for complete search history.

(56) References Cited

U.S. PATENT DOCUMENTS

| | | | |
|---|---|---|---|
| 9,886,867 B2 | 2/2018 | Baphna | |
| 10,832,583 B2 | 11/2020 | Bouillet | |
| 2007/0281287 A1 | 12/2007 | Marioneaux | |
| 2017/0301255 A1* | 10/2017 | Lee | G16H 40/63 |
| 2018/0308473 A1* | 10/2018 | Scholar | A63F 13/00 |
| 2018/0349483 A1* | 12/2018 | Carlisle | G06F 9/451 |
| 2018/0353108 A1* | 12/2018 | Prate | G06F 9/453 |
| 2019/0172069 A1* | 6/2019 | Eisenzopf | H04M 3/5175 |
| 2019/0336314 A1* | 11/2019 | Sedghi | A61F 5/0089 |
| 2022/0374812 A1 | 11/2022 | Riedl | |

FOREIGN PATENT DOCUMENTS

| | | |
|---|---|---|
| WO | 2008/128132 A2 | 10/2008 |
| WO | 2022/263722 A1 | 12/2022 |

OTHER PUBLICATIONS

Ishihara, How far has the molecular alignment of liquid crystals been elucidated?, (journal), Aug. 22, 2005, Journal of Display Technology, vol. 1, Issue: 1, Sep. 2005, p. 30-40, IEEE.
Teguar 15" Medical All-in-One Used with Lung Ventilation Machine; (Webpage); https://www.e3displays.com/new-touch-screen-LCD-display-enhancements-for-medical-ventilators/.

* cited by examiner

*Primary Examiner* — Eliza A Lam
(74) *Attorney, Agent, or Firm* — Caldwell Intellectual Property Law

(57) ABSTRACT

An apparatus for post action planning comprising a memory containing instructions configuring a processor to receive user experience data, identify a learning datum as a function of the user experience data, generate growth data, determine a post action plan as a function of the learning datum and the growth data comprising, receiving post action training data comprising a plurality of the growth data and a plurality of the learning datum correlated to a plurality of post action plans, training a post action machine learning model as a function of the post action training data, and generating the post action plan as a function of the post action machine learning model, create a user interface data structure, wherein the user interface data structure comprises the at least one post action plan; and transmit the at least one post action plan and the user interface data structure.

19 Claims, 8 Drawing Sheets

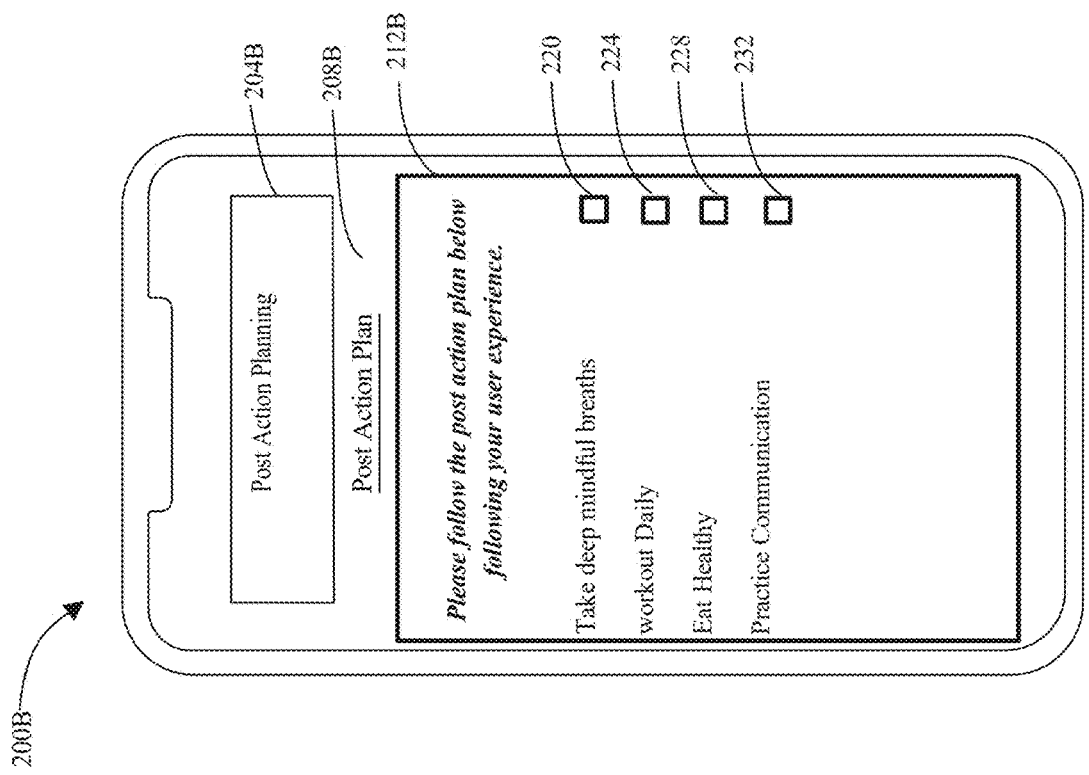
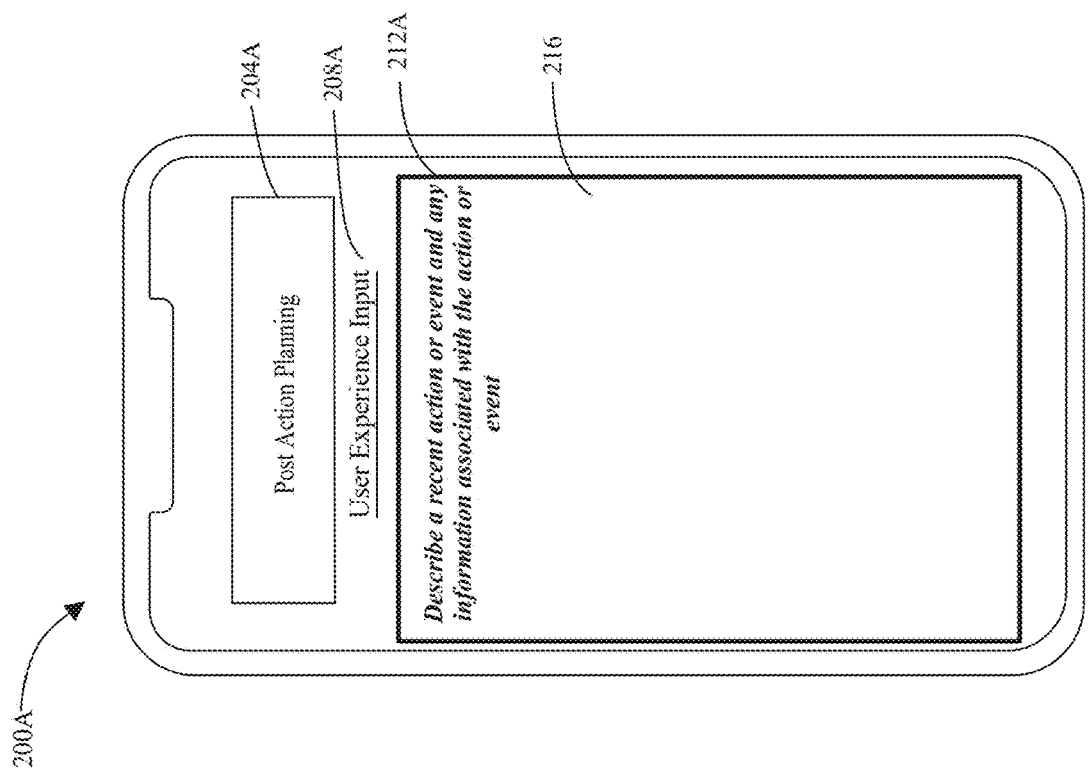
FIG. 2B
FIG. 2A

APPARATUS FOR POST ACTION PLANNING AND METHOD OF USE

FIELD OF THE INVENTION

The present invention generally relates to the field of post action planning. In particular, the present invention is directed to post action planning following a user experience.

BACKGROUND

Post action planning currently is an inaccurate process that cannot effectively determine post action steps or outcomes. Prior attempts to resolve this issue have suffered from inadequate predictive data and insufficient optimal parameters.

SUMMARY OF THE DISCLOSURE

In an aspect an apparatus for post action planning is illustrated. The apparatus includes an input device, the first input device configured to receive user experience data pertaining to a user. The apparatus further includes at least a processor and a memory communicatively connected to the at least a processor, wherein the memory contains instructions configuring the at least a processor to receive the user experience data from the input device, identify at least a learning datum as a function of the user experience data, generate growth data, determine at least one post action plan as a function of the at least a learning datum and the at least a growth data including, receiving post action training data including a plurality of the at least a growth data and a plurality of the at least a learning datum correlated to a plurality of post action plans, training a post action machine learning model as a function of the post action training data and generating the post action plan as a function of the post action machine learning model. The memory further contains instructions configuring the processor to create a user interface data structure, wherein the user interface data structure includes at least one post action plan and transmit the user interface data structure.

In another aspect a method for post action planning is illustrated. The method includes receiving by at least a processor, user experience data pertaining to a user from an input device, and identifying, by the at least a processor, learning datum as a function of the user experience data, generating, by the at least a processor, growth data, the method further includes determining, by the at least a processor, at least one post action plan as a function of the at least a learning datum and the at least a growth data including receiving post action training data comprising a plurality of the at least a growth data and a plurality of the at least a learning datum correlated to a plurality of post action plans, training a post action machine learning model as a function of the post action training data, and generating the post action plan as a function of the post action machine learning model, creating, by the at least a processor, a user interface data structure, wherein the user interface data structure comprises the at least one post action plan, and transmitting, by the at least a processor, the user interface data structure.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 2A-B are an exemplary embodiment of an apparatus for post action planning displayed on a screen;

The drawings are not necessarily to scale and may be illustrated by phantom lines, diagrammatic representations, and fragmentary views. In certain instances, details that are not necessary for an understanding of the embodiments or that render other details difficult to perceive may have been omitted.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for post action planning. In an embodiment, apparatus may include an input device, a memory, a processor, and a graphical user interface. Input device may be used to receive user experience data wherein memory contains instructions configuring processor to receive user experience data.

Aspects of the present disclosure can be used for post action planning, wherein a user may seek to learn from an action or event and improve for the future. Aspects of this disclosure can be used to generate post action plans, predictive growth scores and choose from a plurality of individual post action plans. Exemplary embodiments illustrating aspects of the present disclosure are described below in the context of several specific examples.

Figure 1:
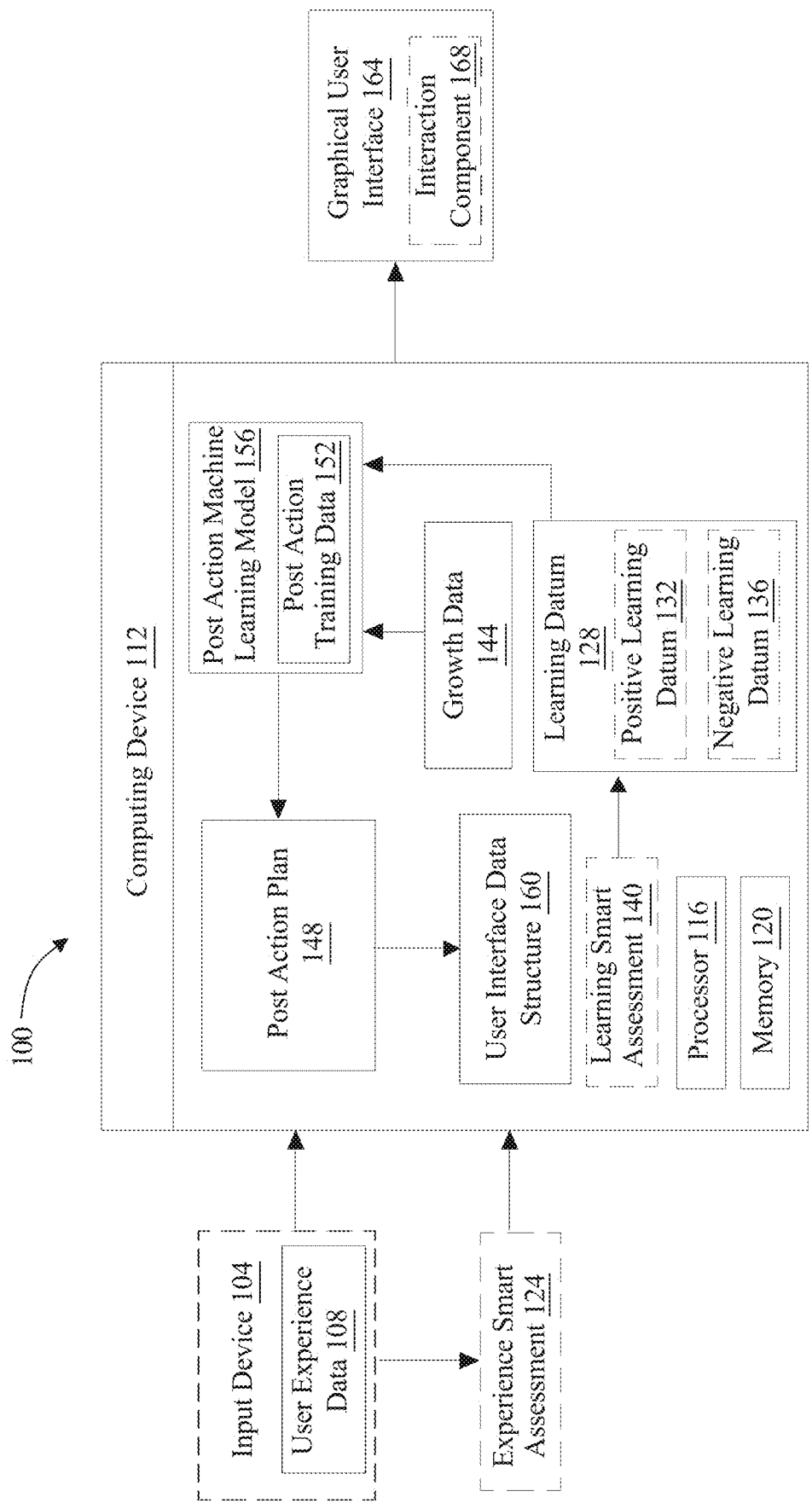
FIG. 1 is a block diagram of an exemplary embodiment of an apparatus for post action planning.

Referring now to FIG. 1, an exemplary embodiment of an apparatus 100 for post action planning is illustrated. Apparatus 100 may include an input device 104. Input device 104 is configured to receive user experience data 108 pertaining to a user. User experience data 108 will be described in further detail below. "Input device" for the purposes of this disclosure is a component capable of providing data to an information processing system such as a computing device as described in this disclosure. Examples of an input device 104 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, a computing device 112 and any combinations thereof. In some embodiments, input device 104 may include at least a camera. As used in this disclosure, a "camera" is a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some embodiments, input device 104 may include a machine vision system that includes at least a camera. A machine vision system may use images from at least a camera, to make a determination about a scene, space, and/or object. For example, in some cases a machine vision system may be used for world modeling or registration of objects within a space. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and ¢ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system may use a classifier, such as any classifier described throughout this disclosure. In some embodiments, input device 104 may include an alpha-numeric input device 104 (e.g., a keyboard), a pointing device, a joystick, a gamepad, an audio input device 104 (e.g., a microphone, a voice response system, etc.), a cursor control device (e.g., a mouse), a touchpad, an optical scanner, a video capture device (e.g., a still camera, a video camera), a touchscreen, and any combinations thereof. Input device 104 may further include a wearable input device, wherein the wearable input device 104 may receive physiological or any other data associated with user such as heart rate, body temperature, body oxygen levels and the like. Input device 104 may further include any device or component capable of receiving audio-visual data. This may include but is not limited to, a computing device, a smartphone, a tablet and the like.

With continued reference to FIG. 1, input device 104 may include a microphone, wherein input device 104 and/or microphone is configured to receive at least audio data. As described in this disclosure "audio data" is data representing sound that is transmitted in signal form such that it may be processed by a computing device. Audio data may include data representing the audio and/or voice of a user, wherein the user speaks into a microphone in order to input user experience data 108. For example, a user may speak their name into a microphone wherein computing device may receive audio data and process audio data into characters that may be displayed on a display. As used in this disclosure, a "microphone" is any transducer configured to transduce pressure change phenomenon to a signal, for instance a signal representative of a parameter associated with the phenomenon. Microphone, according to some embodiments, may include a transducer configured to convert sound into electrical signal. Exemplary non-limiting microphones include dynamic microphones (which may include a coil of wire suspended in a magnetic field), condenser microphones (which may include a vibrating diaphragm condensing plate), and a contact (or conductance) microphone (which may include piezoelectric crystal material). Microphone may include any microphone for transducing pressure changes, as described above; therefore, microphone may include any variety of microphone, including any of: condenser microphones, electret microphones, dynamic microphones, ribbon microphones, carbon microphones, piezoelectric microphones, fiber-optic microphones, laser microphones, liquid microphones, microelectromechanical systems (MEMS) microphones, and/or a speaker microphone. An "audio signal," as used in this disclosure, is a representation of sound. In some cases, an audio signal may include an analog electrical signal of time-varying electrical potential. In some embodiments, an audio signal may be communicated (e.g., transmitted and/or received) by way of an electrically transmissive path (e.g., conductive wire), for instance an audio signal path. Alternatively or additionally, audio signal may include a digital signal of time-varying digital numbers. In some cases, a digital audio signal may be communicated (e.g., transmitted and/or received) by way of any of an optical fiber, at least an electrically transmissive path, and the like. In some cases, a line code and/or a communication protocol may be used to aid in communication of a digital audio signal. Exemplary digital audio transports include, without limitation, Alesis Digital Audio Tape (ADAT), Tascam Digital Interface (TDIF), Toshiba Link (TOSLINK), Sony/Philips Digital Interface (S/PDIF), Audio Engineering Society standard 3 (AES3), Multichannel Audio Digital Interface (MADI), Musical Instrument Digital Interface (MIDI), audio over Ethernet, and audio over IP. Audio signals may represent frequencies within an audible range corresponding to ordinary limits of human hearing, for example substantially between about 20 and about 20,000 Hz. According to some embodiments, an audio signal may include one or more parameters, such as without limitation bandwidth, nominal level, power level (e.g., in decibels), and potential level (e.g., in volts). In some cases, relationship between power and potential for an audio signal may be related to an impedance of a signal path of the audio signal. In some cases, a signal path may single-ended or balanced.

With continued reference to FIG. 1, input device 104 may include a special purpose device. A "special purpose device" for the purposes of this disclosure is a device configured for a unique or particular function. For example, a special purpose device may include a point of sale (POS) device configured to process a user's transactions (i.e., credit score checking, inventory tracking, sale pattern analysis and the like). A special purpose device may include an RFID reader, a sensor, a document scanner, a fax machine, and the like.

With continued reference to FIG. 1, apparatus 100 includes a computing device 112. Computing device 112 and/or apparatus 100 includes at least a processor. Processor 116 may include, without limitation, any processor 116 described in this disclosure. Processor 116 may be included in a computing device. Computing device 112 may include any computing device 112 as described in this disclosure, including without limitation a microcontroller, microprocessor, digital signal processor (DSP) and/or system on a chip (SoC) as described in this disclosure. Computing device 112 may include, be included in, and/or communicate with a mobile device such as a mobile telephone or smartphone. Computing device 112 may include a single computing device 112 operating independently or may include two or more computing device 112 operating in concert, in parallel, sequentially or the like; two or more computing devices may be included together in a single computing device 112 or in two or more computing devices. Computing device 112 may interface or communicate with one or more additional devices as described below in further detail via a network interface device. Network interface device may be utilized for connecting computing device 112 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 112 may include but is not limited to, for example, a computing device 112 or cluster of computing devices in a first location and a second computing device 112 or cluster of computing devices in a second location. Computing device 112 may include one or more computing devices dedicated to data storage, security, distribution of traffic for load balancing, and the like. Computing device 112 may distribute one or more computing tasks as described below across a plurality of computing devices of computing device, which may operate in parallel, in series, redundantly, or in any other manner used for distribution of tasks or memory 120 between computing devices. Computing device 112 may be implemented, as a non-limiting example, using a "shared nothing" architecture.

With continued reference to FIG. 1, computing device 112 may be designed and/or configured to perform any method, method step, or sequence of method steps in any embodiment described in this disclosure, in any order and with any degree of repetition. For instance, computing device 112 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 112 may perform any step or sequence of steps as described in this disclosure in parallel, such as simultaneously and/or substantially simultaneously performing a step two or more times using two or more parallel threads, processor 116 cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 112 may perform determinations, classification, and/or analysis steps, methods, processes, or the like as described in this disclosure using machine-learning processes. A "machine-learning process," as used in this disclosure, is a process that automatedly uses a body of data known as "training data" and/or a "training set" (described further below in this disclosure) to generate an algorithm that will be performed by a processor 116/module to produce outputs given data provided as inputs; this is in contrast to a non-machine learning software program where the commands to be executed are determined in advance by a user and written in a programming language. A machine-learning process may utilize supervised, unsupervised, lazy-learning processes and/or neural networks, described further below.

With continued reference to FIG. 1, apparatus 100 includes a memory 120 communicatively connected to processor. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 120 contains instructions configuring the at least a processor 116 to receive user experience data 108 from input device. "User experience data," for the purposes of this disclosure, is defined as any data relating to actions or events that are associated with a user. This may include, but is not limited to, a previous interaction a user had with another individual, an embarrassing event, a challenging event and the like. User experience data 108 may include data relating to an embarrassing event (e.g., slipping in a crowded area, slurring words during a presentation, forgetting to tie shoes, an uncomfortable conversation with another individual, a wardrobe mishap, and the like. User experience data 108 may further include data relating to a challenging event (e.g., loss of a loved one, raising a child, arguing with a spouse, experiencing abuse, losing a job, getting sued losing a business, divorce, and the like). User experience data 108 may further include data relating to the previous health of a user (e.g. weight gain, preventable health issues caused by an unhealthy lifestyle, a recently given diagnosis, a series of treatments the user has undergone, and the like). User experience data 108 may further include data relating to the interactions of a user (e.g. previously spoken conversations, issues with maintaining a proper conversation, issues with verbalizing a person's needs properly, issues relating to difficult conversations that took place, social anxiety and the like). User experience data 108 may further include a user's experience in relation to a user's fears (an upcoming event of a user wherein the user has a fear of speaking, an upcoming flight wherein a user has a fear of flying, an upcoming ski trip, wherein a user has a fear of skiing, and the like). User experience data 108 may further include data relating to a user's finances (e.g., spending history, gambling addictions, current financial situation, previous financial situations, and the like). User experience data 108 may further include physiological data (e.g. previous heart rates, oxygen levels, vitamin levels and the like). User experience data 108 may further include current or previous mental health of a user (e.g. depression, loneliness, sadness, happiness, feeling of lethargy, and the like). User experience data 108 may further include any significant life event with respect to a user. This may include life events that are not significant to an ordinary person but may be important to a particular user. User experience data 108 may further include any action or even in which a user may seek to learn or grow from. User experience data 108 may further include a "contextual background" of the event. Contextual background for the purposes of this disclosure is the acts or circumstances surrounding the action or event. This may include any data describing the circumstances of the event, such as the age of the user, the user's history with regards to a specific action or event, and the like.

With continued reference to FIG. 1, user experience data 108 may include data in the form of audio, text, images, audio-visual data, and the like. In some cases, user experience data 108 may include a user's search history on from computing device, internet browser or website. In some cases, user experience data 108 may include financial documents, such as previous spending history, credit card transactions and the like. In some cases, user experience data 108 may include screenshots of conversations, actions or activities that were taken on a computing device. In some cases, user experience data 108 may include data captured from virtual environments. Virtual environment may include a plurality of devices connected through networks. In a non-limiting example, apparatus 100 may be configured to receive user experience data 108 from the internet. Such user experience data 108 may include data from social media posts, feeds, browsing histories, and the like thereof. Apparatus 100 may utilize a web crawler to collect user experience data 108 in the virtual environment. Apparatus 100 may be configured to extract an action pattern, wherein the action pattern refers to a set of behaviors or actions taken by a user when interacting with the apparatus 100.

With continued reference to FIG. 1, receiving user experience data 108 from input device 104 may further include processing user experience data 108. "Processing" for the purposes of this disclosure refers to the conversion, maintenance, or modification of data such that the data may be properly used by a computing device. For example, processing user experience data 108 may include compression by inter-frame coding as described in this disclosure. Processing user experience data 108 may further include converting user experience data 108 into text-based data. Computing device 112 may use "speech to text" or "Automatic speech recognition" in order to convert audio data inputted by a user into text data that may be used later on by computing device. "Automatic speech recognition (ASR)" also known as "speech recognition" or "speech to text" is a computer algorithm that may receive an input of audio data, wherein the audio data may include any recognizable sounds and convert those sounds into text based data. For example, a computing device 112 may output text data indicating that a car horn was heard in the audio-visual data. In another non limiting example, a computing device 112 may output speech related to a conversation that was recorded within the audio-visual data. A computing device, such as the one mentioned herein may receive audio or audio-visual data, beak down the audio data into a plurality of phonemes, determine a sequence of the phonemes, compare the sequence to a plurality of sequence, and output a text based on the comparison of the plurality of sequences. ASR algorithms may use a plurality of algorithms to convert speech to text. This may include, but is not limited to hidden Markov models, dynamic time warping based speech recognition, neural networks, machine learning algorithms any other algorithms that may convert text to speech. In some cases, receiving user experience data 108 may include transmitting user experience data 108 to an ASR device, wherein the ASR device is a device configured to convert audio data to speech. In some cases, the ASR device is communicatively connected to computing device. In some cases, the ASR device is wired or wirelessly connected to computing device. In some cases, computing device 112 includes ASR device. In some cases, ASR device may be connected to a network, wherein computing device 112 may transmit user experience data 108 to the network for processing. In some cases, ASR device is a preprogrammed device capable of speech to text recognition. In some cases, computing device 112 may implement already existing speech to text software or algorithms. Additionally, or alternatively, receiving user experience data 108 may include receiving text data from an ASR device.

With continued reference to FIG. 1, database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, user experience data 108 may be derived from a web crawler. A "web crawler," as used herein, is a program that systematically browses the internet for the purpose of Web indexing. The web crawler may be seeded with platform URLs, wherein the crawler may then visit the next related URL, retrieve the content, index the content, and/or measures the relevance of the content to the topic of interest. In some embodiments, computing device 112 may generate a web crawler to scrape user experience data 108 from a plurality of social media sites, blogs, or forums. The web crawler may be seeded and/or trained with a reputable website, such facebook.com, to begin the search. A web crawler may be generated by processor 116. In some embodiments, the web crawler may be trained with information received from an external user through a user interface. In some embodiments, the web crawler may be configured to generate a web query. A web query may include search criteria received from a user. For example, a user may submit a plurality of websites for the web crawler to search to user data statistics from and correlate to pecuniary user data, educational user data, social user data, and the like. Additionally, the web crawler function may be configured to search for and/or detect one or more data patterns. A "data pattern" as used in this disclosure is any repeating forms of information. A data pattern may include repeating pecuniary strategies, educational strategies, and the like. In some embodiments, the web crawler may be configured to determine the relevancy of a data pattern. Relevancy may be determined by a relevancy score. A relevancy score may be automatically generated by processor 116, received from a machine learning model, and/or received from the user. In some embodiments, a relevancy score may include a range of numerical values that may correspond to a relevancy strength of data received from a web crawler function. As a non-limiting example, a web crawler function may search the Internet for user experience data 108 related to an external user. The web crawler may return user experience data 108, such as, as non-limiting examples, user experience data for the purposes of this disclosure.

With continued reference to FIG. 1, receiving user experience data 108 may further include processing user experience data 108 using an image classifier. An "image classifier," as used in this disclosure is a machine-learning model, such as a mathematical model, neural net, or program generated by a machine-learning algorithm known as a "classification algorithm," as described in further detail below, that sorts inputs of image information into categories or bins of data, outputting the categories or bins of data and/or labels associated therewith. Image classifier may be configured to output at least a datum that labels or otherwise identifies a set of images that are clustered together, found to be close under a distance metric as described below, or the like. Computing device 112 and/or another device may generate image classifier using a classification algorithm, defined as a process whereby computing device 112 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. In some cases, processor 116 may use an image classifier to identify a key image in user experience data 108. As used herein, a "key image" is an element of visual data used to identify and/or match elements to each other. An image classifier may be trained with binarized visual data that has already been classified to determine key images in user experience data 108. "Binarized visual data" for the purposes of this disclosure is visual data that is described in binary format. For example, binarized visual data of a photo may be comprised of ones and zeroes wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive an input of user experience and output a key image of user experience data 108. An identified key image may be used to locate a data entry relating to the image data in user experience data 108, such as an image depicting a significant event. In an embodiment, image classifier may be used to compare visual data in user experience data 108 with visual data in another data set, such as previously inserted user experience data 108. In the instance of a video, processor 116 may be used to identify a similarity between videos by comparing them. Processor 116 may be configured to identify a series of frames of video. The series of frames may include a group of pictures having some degree of internal similarity, such as a group of pictures having similar components, scenery, location and the like depicted within them or similar color profiles. In some embodiments, comparing series of frames may include video compression by inter-frame coding. The "inter" part of the term refers to the use of inter frame prediction. This kind of prediction tries to take advantage from temporal redundancy between neighboring frames enabling higher compression rates. Video data compression is the process of encoding information using fewer bits than the original representation. Any compression may be either lossy or lossless. Lossless compression reduces bits by identifying and eliminating statistical redundancy. No information is lost in lossless compression. Lossy compression reduces bits by removing unnecessary or less important information. Typically, a device that performs data compression is referred to as an encoder, and one that performs the reversal of the process (decompression) as a decoder. Data compression may be subject to a space-time complexity trade-off. For instance, a compression scheme for video may require expensive hardware for the video to be decompressed fast enough to be viewed as it is being decompressed, and the option to decompress the video in full before watching it may be inconvenient or require additional storage. Video data may be represented as a series of still image frames. Such data usually contains abundant amounts of spatial and temporal redundancy. Video compression algorithms attempt to reduce redundancy and store information more compactly.

With continued reference to FIG. 1, receiving user experience data 108 may further include processing user experience data 108 using optical character recognition. Optical character recognition or optical character reader (OCR) includes automatic conversion of images of written (e.g., typed, handwritten or printed text) into machine-encoded text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases, a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component. In some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text. In some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 2-4. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 2-4. In some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, OCR may be used to process data such as PDF files, images containing texts, lists of credit card transactions, documents indicating financial history and any other files or documents that may contain text. Computing device 112 may then convert the files mentioned above into text-based data that may be used for data manipulation later on, With continued reference to FIG. 1, receiving user experience data 108 may include receiving user experience data 108 through an experience smart assessment 124. As used in this disclosure, a "smart assessment" is a set of requests or questions that asks for a user's information, such as user experience data 108, wherein each question contains requests that are specific to the particular data that is being requested. For example, a financial smart assessment may contain questions that are geared towards one's finances, whereas an activity smart assessment may contain questions geared towards one's activities. An "experience smart assessment" for the purposes of this disclosure is a smart assessment that is configured to receive user experience data 108. For example, experience smart assessment may include questions or prompts such as "explain your recent experience in detail", "how did the experience make you feel?", "at the moment, what actions did you take?" and the like. In some embodiments, questions or prompts within smart assessment contain open ended questions, or a free input, in which a user is required to answer. In some embodiments, Smart assessment may include a question or prompt followed by a plurality of answers in which a user may select from. The plurality of answers may be chosen from a drop-down menu, the plurality of answers may be a range of answers, in which a user may be required to select the range that falls within their desired input. In some embodiments, plurality of answers may contain a sliding scale in which a user may slide the scale to the preferred numerical result. In a non-limiting example, smart assessment may include a question asking the user a question regarding a recent experience of a user; wherein the question may ask "How did you feel after the action?". Continuing in the example, the user may input their emotion from a plurality of answers. In some embodiments, Smart assessment may take the form of an interview, a report, an interactive software, a virtual meeting or interview, event monitoring, and the like thereof. In some embodiments, smart assessment may include data submission of one or more documentations from the user as described above. In some cases, smart assessment may include a chatbot. For the purposes of this disclosure a "chatbot" is a computer program that simulates and processes human conversation. Chatbot may interact with a user in order to receive user experience data 108. In some cases, chatbot may simulate a human in order to receive user experience data 108 through a conversation that occurred with the user. As opposed to ordinarily typing in information, a chatbot may engage and stimulate a user such that a user may properly input information and not feel bored or discouraged from doing so. Chatbot is descried in further detail below. In some cases, smart assessment may include a plurality of questions or requests wherein the plurality of questions or requests are related to a plurality of topics related to user experience data 108 or any other data as described in this disclosure.

Still referring to FIG. 1, smart assessment may include one or more event handlers. An "event handler" as used in this disclosure is a callback routine that operates asynchronously once an event takes place. Event handlers may include, without limitation, one or more programs to perform one or more actions based on user input, such as generating pop-up windows, submitting forms, requesting more information, and the like. For example, an event handler may be programmed to request more information or may be programmed to generate messages following a user input. User input may include clicking buttons, mouse clicks, hovering of a mouse, input using a touchscreen, keyboard clicks, an entry of characters, entry of symbols, an upload of an image, an upload of a computer file, manipulation of computer icons, and the like. For example, an event handler may be programmed to generate a notification screen following a user input such as inputting characters into a computer. In some embodiments, an event handler may be programmed to request additional information after a first user input is received. In some embodiments, an event handler may be programmed to generate a pop-up notification when a user input is left blank. In some embodiments, an event handler may be programmed to generate requests based on the user input.

With continued reference to FIG. 1, memory 120 further contains instructions configuring processor 116 to identify at least a learning datum 128 as a function of user experience data 108. "Learning datum" for the purposes of this disclosure is data relating to an educational understanding of an action or event as described above and/or in user experience data 108. "Educational understanding" for the purposes of this disclosure is knowledge and/or insights with regards to a specific action or event that may allow one to make more informed decisions in the future. For example, a user may have and educational understanding of an embarrassing event, wherein the user may make informed decisions or actions in similar future events. Learning datum 128 may refer to knowledge and/or actions about particular events that occurred or are associated with events or actions in user experience data 108. In some embodiments, learning datum 128 may include data related to users' previous knowledge, skill level, learning preference, learning environment, learning methodology, instructional material, used assessment tool, and the like in performing actions, identified from user experience data 108. In some cases, learning datum 128 may include the actions or steps taken during the event. For example, learning datum 128 may indicate how a user responded to a specific event and what they learned after the event. In a more specific example, learning datum 128 may include a user's mischaracterizations during a financial event that ended in financial loss. Continuing the example, learning datum 128 may further include what the user had learned as a result of the mischaracterization and the financial loss. In some cases, learning datum 128 may include positive learning datum 132. "Positive learning datum" for the purposes of this disclosure is a learning datum configured to enhance the learning experience of a user. In some embodiments, positive learning datum 132 may include various types of data that indicate progress or success in performing actions described above. For example, positive learning datum 132 may include data relating to increased financial awareness, increased financial security, or increased financial wealth as a result of an action or event involving finances. Positive learning datum 132 may include any positive action, experience, or result of occurred as a result of a user experience in user experience data 108. In some embodiments, learning datum 128 may include negative learning datum. "Negative learning datum" for the purposes of this disclosure is learning datum 128 configured to identify areas where the user is struggling or experiencing difficulty. In some embodiments, negative learning datum 136 may include various types of data that indicate a lack of progress or understanding, gaps in knowledge or skills, and the like in performing actions described above. In some cases, negative learning datum 136 may further include negative repercussions as a result of an action or event as described above. In a non-limiting example, negative learning datum 136 may include decreased health, decreased health awareness and the like in relation to an action or event involving health. In some cases, identifying at least a learning datum 128 may include receiving learning datum 128 from a user. Learning datum 128 may be received by an input device 104 as described above. Learning datum 128 may be received through any means and through any input device 104 as described above.

With continued reference to FIG. 1, identifying learning datum 128 as a function of user experience data 108 may further include identifying learning datum 128 within user experience data 108. For example, user experience data 108 may include data which may indicate that a user has an increased financial awareness as a result of the action or event wherein computing device 112 may identify the increase in financial awareness as learning datum 128. Learning datum 128 may be identified using a classifier. A classifier may be configured to output learning datum 128 that labels or otherwise identifies a set of data that are clustered together, found to be close under a distance metric as described below, or the like. For example, a classifier may receive user experience data 108 and output a label that can be used to categorize user experience data 108 into bins or categories, such as a learning category and/or a positive learning category and/or a negative learning category. Learning datum may then include data associated with one or more groupings within user experience data. Processor 116 may generate the classifier using a classification algorithm, which may include a process whereby a processor 116 derives a classifier from training data. Training data may include a plurality of user experience data that is correlated to a plurality of step classes. "Step class" for the purposes of this disclosure is a grouping of data relating to each sequence of events surrounding the action or event an event. As a non-limiting example, step class may include a pre-action category (for example this may include actions taken before the event), an action category (for example this may include the actions taken during the event), a post action category (for example this may include actions taken after the event) a learning category (for example this may include what a user may have learned), a growing category (for example this may include how the user grew as a result of the event), an effect category (for example this may include what effects results due to the action or event) and the like. In an embodiment, training data may indicate that particular elements within user experience data may be correlated to particular step classes. In an embodiment, training data may correlate elements within user experience data to a learning category, wherein the elements within the learning category may be added to learning datum 128. In an embodiment, data associated with one or more grouping of elements within user experience data may comprise learning datum 128. In some cases, learning datum may include data within user experience data that has been classified into learning categories. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. In some cases, identifying learning datum 128 as a function of user experience data 108 may include using a text search algorithm and/or a string search algorithm (also known as a string match algorithm) to identify a plurality of trigger words, or strings (a sequence of characters used to represent text), wherein the plurality of trigger words or strings may be used to "search" for learning datum. For example, text search algorithm may contain a string such as "more money" wherein the string present within user experience data 108 may indicate that a user has increased financial security. A text search algorithm may be used to search for key words or trigger words wherein the key words or trigger words may be used to identify learning datum 128 within user experience data 108. In another non-limiting example, a key word or trigger word of "bruised" or "hurt" may indicate that a user was hurt as a result of the action or event. This experience may be categorized as negative learning datum 136 wherein a user struggled or faced difficulty. As used herein a "trigger word" or "key word" is a word or a particular sequence of words that may be searched for in a given data. For example, a text search algorithm may include a trigger word such as "depressed" or "depression" wherein the presence of such a trigger word within user experience data 108 may signify that a user had a negative experience. Text search algorithm may include a plurality of trigger words wherein each trigger word may be associated with learning datum. The trigger words may be input by a user such as a life coach, an ordinary user, a third party or any party that has an interest in apparatus 100. The trigger words may be retrieved from a database. In some cases, the trigger words may be generated based on previous iterations. In some cases, learning datum 128 may include an intensity score wherein the intensity score indicates how prevalent a particular trigger word is. For example, the presence of a particular string such as "sad" found multiple times with user experience data 108 may indicate that a user has heightened negative emotions as a result of a particular event. As a result, data relating to heightened negative emotions may have a higher intensity score within learning datum. Intensity score may be generated based on predetermined data that correlates the presence of a particular word and the number of times it is mentioned to a particular score. For example, predetermined data may indicate that the presence of the word "sad" between 10 and 12 times within user experience data 108 may correlate to an intensity score of 70 wherein the score is calculated on a range of 1-100.

With continued reference to FIG. 1, identifying learning datum 128 as a function of user experience data 108 may include receiving the at least a learning datum 128 from a user through a learning smart assessment 140. "Learning smart assessment" for the purposes of this disclosure is a smart assessment configured to receive learning datum. Learning smart assessment 140 may include questions, surveys or prompts related to learning datum. As described above, user may input data through a series of questions and the like within learning smart assessment. Generating learning smart assessment 140 as a function of user experience data 108 may include classifying user experience data 108 to one of a plurality of experience categories and generating at least one learning smart assessment 140 as a function of the user experience data 108 and one of the plurality of experience categories. Additionally or alternatively, learning smart assessment 140 may be generated as a function of user experience data 108, wherein a particular set of questions within learning smart assessment 140 may be chosen from a plurality of questions, wherein the particular set of questions may relate to the activity or event described in user experience data 108. For example, learning smart assessment 140 may include questions relating to job loss when user experience data 108 indicates that a user recently lost their job. Computing device 112 may choose the particular set of questions by classifying data within user experience data 108 to a particular group, wherein each particular group may be associated with a particular set of questions. For example, when elements of user experience data 108 are classified to a job loss group, learning smart assessment 140 may include questions relating to job loss such as "what did you do after you lost your job?" and "how did you budget after losing your job?". Learning smart assessment 140 may be generated by selecting questions from a database containing a plurality of questions. The plurality of questions may be generated by a user, previous iterations and any other way as described in this disclosure.

A classifier may be configured to output an event category that labels or otherwise identifies a set of data that are clustered together, found to be close under a distance metric as described below, or the like. For example, a classifier may receive user experience data 108 and output datum that can be used to categorize data within user experience data 108 into bins or categories, such a financial category, a health category, a job loss category and the like. Questions may then be retrieved using a lookup table. A "lookup table" for the purposes of this disclosure is an array of predetermined values wherein each value may be looked up using a key corresponding to that specific value. For example, a category pertaining to a financial event may contain data within a lookup table of question relating to the particular event. The lookup table may be retrieved from a database and/or generated by a user. In some embodiments, at least a processor 116 may 'lookup' a given category to one or more lists of questions. Processor 116 may generate the classifier using any algorithm for the purposes of this disclosure. In some cases, generating the learning smart assessment 140 as a function as a function of user experience data 108 includes generating learning smart assessment 140 using a machine learning model.

Still referring to FIG. 1, a "classifier" as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 112 and/or another device may generate a classifier using a classification algorithm, defined as a process whereby a computing device 112 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Further referring to FIG. 1, processor 116 and/or computing device 112 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)=P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 112 may then calculate a likelihood table by calculating probabilities of different data entries and classification labels. Computing device 112 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, processor 116 and/or computing device 112 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process for the purposes of this disclosure. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors for the purposes of this disclosure may be scaled, such that each vector represents each attribute along an equivalent scale of values. Each vector may be "normalized," or divided by a "length" attribute, such as a length attribute/as derived using a Pythagorean norm: $l=\sqrt{\Sigma_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Continuing to reference FIG. 1, processor 116 may use a machine learning module, such as a machine learning module for the purposes of this disclosure, to implement one or more algorithms or generate one or more machine-learning models, such as an assessment machine learning model, to calculate at least one smart assessments. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from a database, such as any database described in this disclosure, or be provided by a user. In other embodiments, a machine-learning module may obtain a training set by querying a communicatively connected database that includes past inputs and outputs. Training data may include inputs from various types of databases, resources, and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements. A machine learning module, such as assessment module, may be used to generate assessment machine learning model and/or any other machine learning model using training data, assessment machine learning model may be trained by correlated inputs and outputs of training data. Training data may be data sets that have already been converted from raw data whether manually, by machine, or any other method. Assessment training data may be stored in a database. Assessment training data may also be retrieved from database.

With continued reference to FIG. 1, in some cases, identifying the at least a learning datum 128 as a function of the user experience data 108 further includes receiving the at least a learning datum 128 from a user through learning smart assessment, the learning smart assessment 140 generated as a function of the user experience data 108. Generating learning smart assessment 140 as a function of user experience data 108 may include generating learning smart assessment 140 using a machine learning model. Generating learning smart assessment 140 as a function of user experience data 108 may include receiving assessment training data. In an embodiment, assessment training data may include a plurality of user experience data 108 correlated to a plurality of learning smart assessments. For example, assessment training data may be used to show a particular user experience data 108 is correlated to one of a plurality of learning smart assessments, wherein each of the plurality of learning smart assessment 140 contain questions relating to a particular category or topic related to user experience data 108. In an embodiment, learning smart assessment 140 may be used to ask questions, conduct surveys, or request responses that are specific to a particular event. In some embodiments, assessment training data may be received from a user, third party, database, external computing devices, previous iterations of processing, and/or the like as described in this disclosure. Assessment training data may further be comprised of previous iterations of user experience data 108 and/or previous learning smart assessments. Assessment training data may be stored in a database and/or retrieved from a database. Generating assessment training data may further include training an assessment machine learning model as a function of assessment training data and generating learning smart assessment 140 as a function of assessment machine learning model. In some cases, assessment training data may be trained through user input wherein a user may determine if learning smart assessment 140 is accurate and/or applicable to the current event or activity.

With continued reference to FIG. 1, identifying the at least a learning datum 128 may include identifying the at least a learning datum 128 using a machine learning model. Identifying learning datum 128 as a function of user experience data 108 may include receiving learning training data. In an embodiment, learning training data may include a plurality of user experience data 108 correlated to a plurality of learning datum. For example, learning training data may be used to show a particular user experience data 108 is correlated to one of a plurality of learning datum, wherein each of the plurality of learning datum 128 contains education data relating to the experience of a user of a particular activity. In an embodiment, learning datum 128 may be used to determine what education aspects resulted as a result of a particular action or event. In some embodiments, learning training data may be received from a user, third party, database, external computing devices, previous iterations of processing, and/or the like as described in this disclosure. Learning training data may further be comprised of previous iterations of user experience data 108 and/or learning datum. Learning training data may be stored in a database and/or retrieved from a database. Generating learning training data may further include training a learning machine learning model as a function of learning training data and identifying learning datum 128 as a function of learning datum 128 learning model. In some cases, learning training data may be trained through user input wherein a user input may determine if learning datum 128 is accurate and/or applicable to the current event or activity.

With continued reference to FIG. 1, memory 120 further contains instructions configuring the at least a processor 116 to generate growth data. "Growth data" as used herein is data relating to the improvement and/or data relating to the response of a user following an action or event within user experience data 108. For example, growth data 144 may include the progress of a user over time, such as, for example, the financial literacy of a user over a given period of time. In another non-limiting example, growth data 144 may include data pertaining to an analysis on the user's actions and data pertaining to an analysis of their improvements since the action or event. Growth data 144 may be used to track the progress of a user following an action or event. In some embodiments, growth data 144 may include data related to improvement or advancement of user performance on one or more actions; for instance, and without limitation, increased scores on an assessment, completion of more difficult tasks, mastery of more complex skills and the like. Growth data 144 may further include steps taken to improve a specific action or event. In some cases, Growth data 144 may further include optimal output datum. "Optimal output datum" for the purposes of this disclosure is datum or data describing an optimal response associated with the action or event described in user experience data 108. For example optimal output datum may indicate an optimal response associated with a financial event such as, filing taxes properly during the financial event. In another non-limiting example, optimal output datum may indicate proper behavior during an action or event such as during the firing of an employee or during a sensitive conversation. Optimal output datum may indicate how an event should have been handled based on user experience data 108 and learning datum 128. Optimal output datum may be used to indicate to a user the proper response that should have been taken during the action or event. Generating growth data 144 may include generating growth data 144 as a function of user experience data 108. In an embodiment, computing device 112 may generate growth data 144 based on the data present in user experience data 108. For example, computing device 112 may use speech to text recognition and the like as described above to find trigger words that relate to the growth of a user within user experience data 108. For example, computing device 112 may search for words or strings indicating that a user has been improving in various area. In some cases, growth data 144 may include a growth score. As described in this disclosure, "growth score" is data indicating the growth of a user. Growth score may indicate how well a particular user handled a specific action or event. Growth score may include a numerical score such as a score of 1-100 wherein 1 may signify that a user has had little growth since the event and a higher score may signify that a user had more growth since the event. In some cases, growth score may be generated as a comparison between growth data 144 and optimal output datum, wherein growth score determines a degree of similarity between growth data and optimal output datum. The degree of similarity may signify how properly an event was handled wherein a low degree of similarity in growth score may indicate that an event was not properly handled whereas a high degree of similarity within growth score may indicate that an event was properly handled. Growth score may be used to indicate how well a user handled a particular event. In some cases, generating growth data 144 may include receiving growth data 144 from a user. A user may input growth data 144 indicating the growth that was achieved since the action or event. This may include, taking courses, increasing skill in a particular area, recovering from an action or event and the like. In addition, a user may input optimal output datum wherein a user may input what should have been done now that the event or action has concluded. Growth data 144 may further be generated through a smart assessment wherein a user may score themselves, and answer questions and the like related to their growth in a particular area. A smart assessment may include questions and/or prompts asking a user to score a user's progress. In some cases, growth data may include multiple elements of growth, for example, growth in different areas, wherein a user may be asked to score each particular area. In some cases, growth data 144 may be generated as a function of user experience data 108 wherein growth data 144 is generated using a machine learning model as described in this disclosure. In some cases, growth data 144 may be generated using any algorithm as described in this disclosure. In some cases, a machine learning model may include a classifier configured to classify user experience data 108 to a plurality of growth data. In an embodiment, machine learning model may be used to indicate that a particular user experience data is correlated to a particular growth data, wherein the growth data may indicate the growth of a user as a result of the action or event. In an embedment, growth data may indicate a particular growth or a particular optimal output of an action or event within user experience data. In some cases, a classifier may be used to categorize user experience data 108 to a plurality of growth data, wherein the one of the plurality of growth data 144 may indicate the growth of a user. The classifier may be trained using training data having a plurality of user experience data 108 correlated to a plurality of growth data 144. In some cases, generating growth data 144 may include receiving growth data 144 from a database. For example, optimal growth data may be retrieved from a database of a plurality of predetermined data wherein the plurality of predetermined data is data containing a plurality of optical growth data associated with a plurality of actions or events. A specific optimal growth data associated with the action or event in user experience data may be chosen from the plurality of predetermined data.

With continued reference to FIG. 1, memory 120 further contains instructions configuring processor 116 to determine at least one post action plan 148 as a function of the at least a learning datum 128 and the at least a growth data 144. "Post action plan" for the purposes of this disclosure is data including a set of instructions for a user after completion of an action or event. In some embodiments, post action plan 148 may include recommendations, feedback, or personalized instructions for the user based on learning datum 128 and growth data 144. In some embodiments, post action plan 148 may be configured to promote continuous improvement and advancement (e.g., enhance effectiveness, efficiency, skills, and the like) in user's experience in performing one or more actions. Post action plan 148 may include instructions on how to handle or resolve an activity or event. Post action plan 148 may further include instructions on how to prevent activities or events described above. Post action plan 148 may further include instructions on how to navigate activities or events in the future. In some cases, post action plan 148 may further include instructions on how to navigate future events that may occur as a result of the action or event in user experience data 108. Post action plan 148 may further include instructions on how to increase a user's growth score. Post action plan 148 may further include projected growth data wherein projected growth data is a speculated growth data that may be achieved in the future based on implementation of post action plan 148. In some cases, at least one post action plan 148 may contain a plurality of individual action plans. As described in this disclosure an "individual action plan" is a set of instructions for a user with reference to one particular category, such as for example, one particular category within growth data and/or learning datum, wherein post action plan may contain a plurality of individual action plans. A plurality of action plans may contain multiple routes on how a post action plan 148 may be implemented. For example, an individual action plan may include instructions on taking a course, whereas a second individual action plan may include instructions on taking an assessment. A user may be given the opportunity to choose one of the individual action plans, such as whichever individual action plan may be best suited for them. Additionally, or alternatively, each individual action plan may contain a predictive growth score, wherein the predictive score may predict a user's growth based on the implementation of the individual action plan. For example, a first individual action plan may contain a predictive growth score of 70 out of 100 whereas a second individual action plan may contain a predictive growth score of 85 out of a 100. A user may have a choice of choosing between the individual action plans. A user may choose an easier individual action plan that may suit their lifestyle even if the individual action plan contains a lower predictive growth score. In some cases post action plans comprises a plurality of steps, wherein each step may signify a different stage in post action plan. A user may follow the steps sequentially or out of order. In some cases, the plurality of steps must be followed in a sequential order. In some cases, post action plan 148 may further include a checklist wherein a user may check off each individual step that was completed. Additionally, or alternatively each step of the plurality of steps may contain an individual predictive growth score wherein the individual predictive growth score is a predictive score that determines a user's growth after each step. Growth score may be determined based on a predetermined score wherein completion or mastery of each step may indicate a rise in growth score. For example, Knowledge or implementation of 5 out of 10 steps in post action plan 148 may give a user a growth score of 50/100. In some cases, each step or instructions may be given a different weighted amount based on its complexity. In some cases, each step or set of instructions may contain sub score out of 10 wherein mastery of the step may indicate a sub score of 10 and little knowledge or partial completion of the step may indicate a score of 3 or less. Predictive growth score may be calculated based on the plurality of individual predictive growth scores that have been calculated. In some cases predictive growth score may be calculated based on previous iteration in which a similar user underwent a similar action or activity. Predictive growth score may be a predetermined growth score that has been calculated based on previous iterations.

In some cases, determining at least one post action plan 148 may include receiving a plurality of future events. "Plurality of future events" for the purposes of this disclosure is data containing a plurality of actions or events that may are likely to occur in the future following an action or event as described in user experience data 108. For example, plurality of future events may include an event such as a bankruptcy that may follow a financial loss event or action described in user experience data 108. In another non-limiting example, plurality of future events may include an event such as a depressive episode following an action involving a personal crisis. Plurality of future events may further include any consequences that follow a particular action or event. In some cases, plurality of future events may include more than one events that are associated with a particular action or event. For example, a particular action such as financial loss may contain a future event such as bankruptcy and auditing. Plurality of future events may be retrieved from a database as described in this disclosure. In some cases plurality of future events may be inputted by a user, third party or any other person or party that may have an interest in post action planning. Plurality of future events may be generated based on previous events that have occurred as a result of an action or event based on previous iterations. Plurality of future events may be generated by professionals in post action planning, such as life coaches, therapists, trained professions in post action planning and the like. Additionally or alternatively, determining at least one post action plan may further include selecting at least one future event from the plurality of future events. Selecting at least one future event may include classifying at least one future event to an event class. As used in this disclosure an "event class" is a grouping of events based on the particular issue involved. As a non-limiting example, event class may include a financial event, a challenging event, an embarrassing event, and the like as described above. Processor 116 may then output at least one future event based on the classification. Classification may be performed using a classification model as described in this disclosure. Processor 116 may output at least one future event having a similar classification to user experience data 108. For example, at least one future event associated with a financial event class may be outputted when user experience data 108 is associated with a financial event class as well. In some cases, more than one future event may be chosen. In some cases, selecting at least one future events from the plurality of future events may include selecting at least one future event using a machine learning model. Selecting the at least one future event may include receiving future event training data. Future event training data may include a plurality of user experience data correlated to a plurality of future events. In an embodiment, future event training data may be used to show that a particular future event may be associated with user experience data. In some embodiments, future event training data may be received from a user, third party, database, external computing device, previous iterations of the function and/or the like. In some embodiments, future event training data may be stored and/or retrieved from a database. Selecting at least one future event may further include training a future event machine learning model as a function of the future event training data and generating at least one future event as a function of the future event machine learning model. In some embodiments, outputs of future event machine learning model may be used to train future event training data. Additionally or alternatively, determining a post action plan may further include determining a post action plan based on the at least one future event. In a non-limiting example, post action plan may include steps or instructions to prepare for at least one future event. In some cases, post action plan may be generated based on the at least one future event and the learning datum.

With continued reference to FIG. 1, post action plan 148 may be determined by using learning datum 128 and growth data 144 to create post action plan 148 that is geared towards the specific user at hand. For example, learning datum 128 may be used to determine what positive or negative learning experiences a user had and generate a list of instructions to modify those experiences or prevent them from happening in the future. In post action plan 148 may be determined as a function of growth data 144 by using growth data 144 to determine how much a user grew and how much is needed to increase growth. For example, post action plan 148 may contain instructions on how a user can grow and how to increase growth if a user's growth has been low. On the other hand, post action plan 148 may instead only contain instruction on how to maintain growth if the growth of a user is higher. Determining post action plan 148 as a function of the learning datum 128 and growth data 144 may further include classifying learning datum 128 and growth data 144 to a specific category using a classifier as described in this disclosure. Computing device 112 may then use a lookup table having a plurality of post action plans that are each correlated to a specific category. The specific category, generated by computing device 112, within learning datum 128 and post action plan 148 may be used to determine the at least one post action plan. For example, learning datum 128 and growth data 144 may be used to classify a user to a low growth category involving learning datum 128 of a financial event, wherein a post action plan 148 may be chosen that is correlated to a low growth category involving learning datum 128 of a financial event. In some cases, processor 166 may adjust the instructions or steps within post action plan 148 as a function of user experience data and/or growth data. For example, data within user experience data 108 and/or growth data 144 may indicate that a particular step within post action plan 148 may need to be adjusted or altered. Continuing, growth data 144 may indicate that a user has low growth, and as a result, the user may need easier instructions or steps within post action plan 148.

With continued reference to FIG. 1, determining at least one post action plan 148 as a function of at least a learning datum 128 and at least a growth data 144 includes determining at least one post action plan 148 using a machine learning model. Determining at least one post action plan 148 as a function of at least a learning datum 128 and at least a growth data 144 includes receiving post action training data 152. In an embodiment, post action training data 152 may include a plurality of learning datum 128 and a plurality of growth data 144 correlated to a plurality of post action plans. For example, post action training data 152 may be used to show a particular learning datum 128 and growth data 144 that is correlated to one of a plurality of post action plans. In an embodiment, post action plan 148 may be used to instruct a user on how to proceed following an event based on their learning datum 128 and growth data. In some embodiments, post action training data 152 may be received from a user, third party, database, external computing devices, previous iterations of processing, and/or the like as described in this disclosure. Post action training data 152 may further be comprised of previous iteration of learning datum, growth data 144 and post action plan. Post action training data 152 may be stored in a data base and retrieved from a data base. Determining post action plan 148 may further include training a post action machine learning model 156 as a function of post action training data 152 and determining post action plan 148 as a function of post action machine learning model 156. In some cases, post action training data 152 may be trained through user input wherein a user may determine if the post action plan 148 is accurate and/or applicable to the current action or event.

With continued reference to FIG. 1, memory 120 further contains instructions to create a user interface data structure 160. As used in this disclosure, "user interface data structure" is a data structure representing a specialized formatting of data on a computer configured such that the information can be organized, processed, stored, and retrieved quickly and effectively for a user interface. User interface structure includes at least one post action plan. In some cases, user interface data structure 160 further includes any data as described in this disclosure, such as growth data, learning datum, user experience data 108 and the like. Additionally, or alternatively, processor 116 may be configured to generate user interface data structure 160 using any combination of data as described in this disclosure With continued reference to FIG. 1, memory 120 further contains instructions to transmit the at least one post action plan. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. Memory 120 may transmit the data described above to a database wherein the data may be accessed from a database, memory 120 may further transmit the data above to a device display or another computing device.

With continued reference to FIG. 1, apparatus 100 further may include a graphical user interface 164 (GUI) communicatively connected to at least a processor. For the purposes of this disclosure, a "user interface" is a means by which a user and a computer system interact; for example, through the use of input devices and software. A user interface may include graphical user interface, command line interface (CLI), menu-driven user interface, touch user interface, voice user interface (VUI), form-based user interface, any combination thereof and the like. In some embodiments, a user may interact with the user interface using a computing device 112 distinct from and communicatively connected to at least a processor. For example, a smart phone, smart, tablet, or laptop operated by the user and/or participant. A user interface may include one or more graphical locator and/or cursor facilities allowing a user to interact with graphical models and/or combinations thereof, for instance using a touchscreen, touchpad, mouse, keyboard, and/or other manual data entry device. A "graphical user interface,"

as used herein, is a graphical form of user interface that allows users to interact with electronic devices. In some embodiments, GUI 164 may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface, skilled in the art, upon reviewing the entirety of this disclosure, will be aware of various ways in which a graphical user interface 164 and/or elements thereof may be implemented and/or used as described in this disclosure.

With continued reference to FIG. 1, GUI 164 is configured to receive the user interface structure and display at least one post action plan 148 as a function of the user interface data structure 160. GUI 164 may be displayed on a display device. Display device may include, but is not limited to, a smartphone, tablet, laptop, monitor, tablet, and the like. Display device may include a separate device that includes a transparent screen configured to display computer generated images and/or information. In some cases, GUI 164 may be displayed on a plurality of display devices. In some cases, GUI 164 may contain an interaction component 168. As described in this disclosure an "interaction component" 168 is a device and/or program that is configured to allow a user/participant to interact with GUI 164. Interaction component 168 may include a button or similar clickable elements wherein the clicking of the button may initiate a response or a command. In some cases, interaction component 168 may allow a user to select an individual action plan from the plurality of individual action plans present within post action plan. Interaction component 168 may further contain drop down menus where a user may choose from a list of commands wherein the list of commands may perform different functions. For example, a command may include pausing or stopping the data that is being displayed. Interaction feature may further include dialog or comment boxes wherein users may enter comments about data that is displayed. Comment boxes may be consistent with user input, such as a smart assessment, as described above when a user may input user experience data 108, learning datum 128 and/or growth score into a comment box. Interaction component 168 may further allow a user to modify or change data within post action plan. In some cases, interaction component 168 may be used to provide feedback to an operator. In some cases, interaction component 168 may allow a user to provide feedback on post action plan 148 such that machine learning model may be trained to provide better results. In some embodiments, configuring one or more interaction components may include select one or more interaction components properties as a function of the post action plan. In a non-limiting example, an interaction component 168 with a larger size may be selected to display a first instruction of post action plan 148 and another interaction component 168 with a smaller size may be selected to display a second instruction of post action plan, wherein the first instruction may be generated based on learning and/or growth data 144 with a higher score than learning and/or growth data 144 used to generate the second instruction. Other interaction components properties may include, without limitation, color, content, function, animation, and the like thereof.

Referring now to FIGS. 2A-2B an exemplary embodiment of an apparatus for post action planning is illustrated. For example, screen 200A and 200B may display information relating to user experience data and apparatus as described above by way of a smart phone. Screen 200A may be an initial screen having multiple fields such as an identification field 204A identifying the process that will take place. A sub identification field 208A may be used to indicate to a user the type of data being received or displayed. In this instance, "user experience input" is displayed on sub identification field 208A which will indicate to a user that screen may be requesting or displaying user experience data as described above. Screen 200A may further include an instruction field 212A to instruct a user on the type of data desired and/or to describe the data being displayed. In this instance, instruction field 212A may instruct a user to input a recent action or event. This action or event may be collected as user experience data as described above. Screen 200A may include multiple instructions that Are displayed in sequence, wherein each instruction may request various types of data, for example, one instruction may request the age of a user, whereas a second instruction may request details about an action or event. Screen 200A may further include an Input field 216. Input field may be used to receive data or information from a user. A user may input information using an on-screen keyboard on a smart phone or any other input device.

Continuing to refer to FIG. 2B, Screen 200B may display a post action plan to a user following user input in Screen 200A. Identification field 204B may be used to indicate to a user that a user is still within the post action planning module or is still receiving or inputting prompts with respect to post action planning. Sub identification field 208B may change throughout prompts to indicate to a user, that computing device has moved to another process. In this instance sub identification field 208B may indicate that a post action plan or data associated with a post action plan may be displayed on Screen 200B at the moment. Instruction field 212B may instruct a user on the data that is described in post action plan as described in this disclosure. A first post action step 216 may display a step that a user may need to take as part of their post action plan. In this instance, a first post action step 220 may include taking deep mindful breaths. This step may be generated in actions or events that may have a negative impact on a user. Similarly, a second post action step 224 may indicate a second step in a post action plan such as working out daily. A third post action step 228 may indicate a third step in a post action plan such as Eating healthy. A fourth post action step may indicate a fourth step such as practicing communication 232. The steps described herein may be displayed on screen 200B as checklists, wherein a user may check off steps that have been accomplished. A user may further opt out of various steps or complete them out of sequence. It is to be understood that these steps are non-limiting and provided as examples of possible data in a post action plan.

Figure 3:
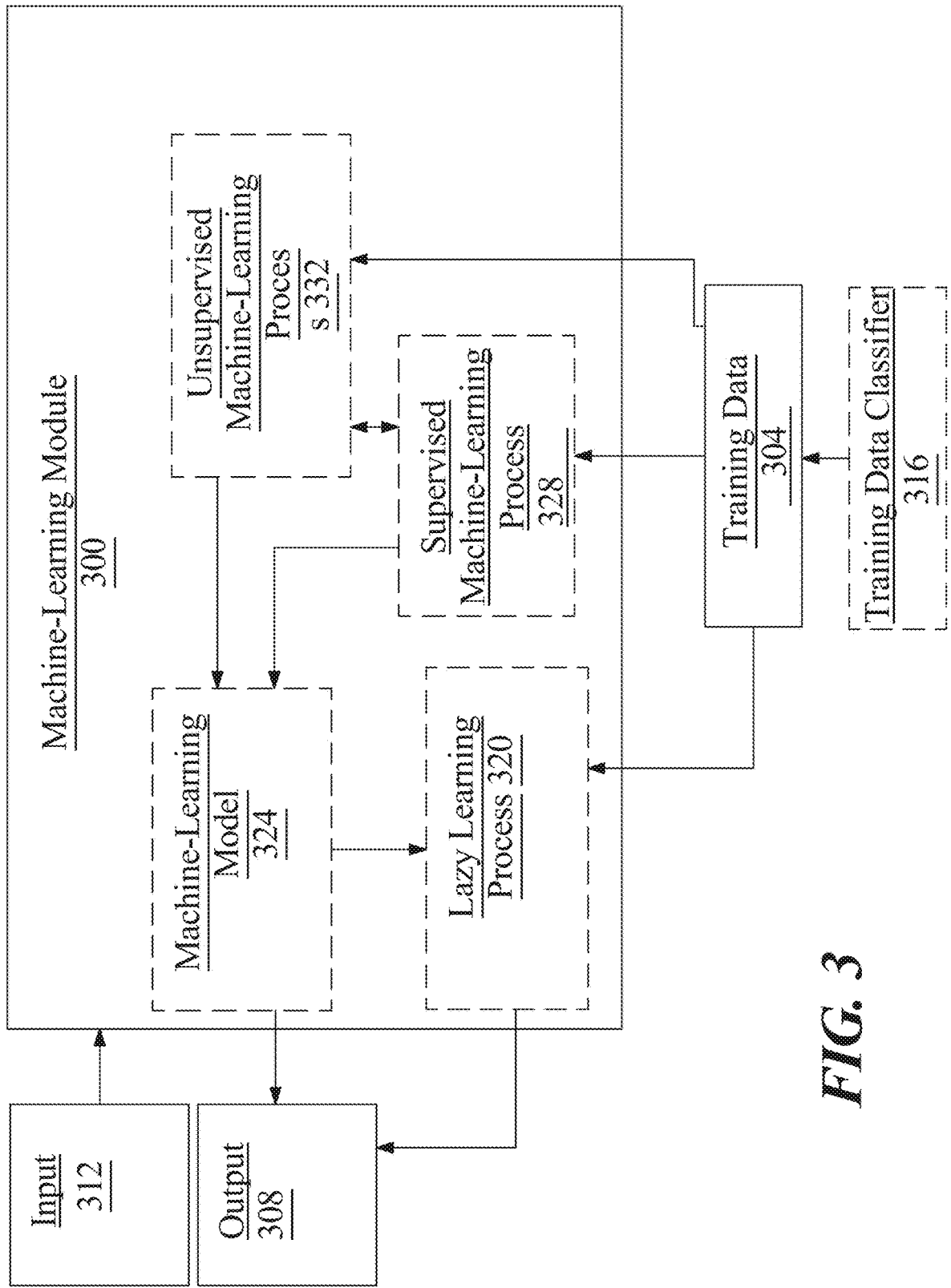
FIG. 3 is a block diagram of exemplary embodiment of a machine learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example, inputs may include inputs such as learning data and output may include post action plan data.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to post action plans and specific types of post action plans and/or other analyzed items and/or phenomena for which a subset of training data may be selected.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include learning datum as described above as inputs, post action plan data as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods.

Machine-learning algorithms may include neural net algorithms, including convolutional neural net processes.

Figure 4:
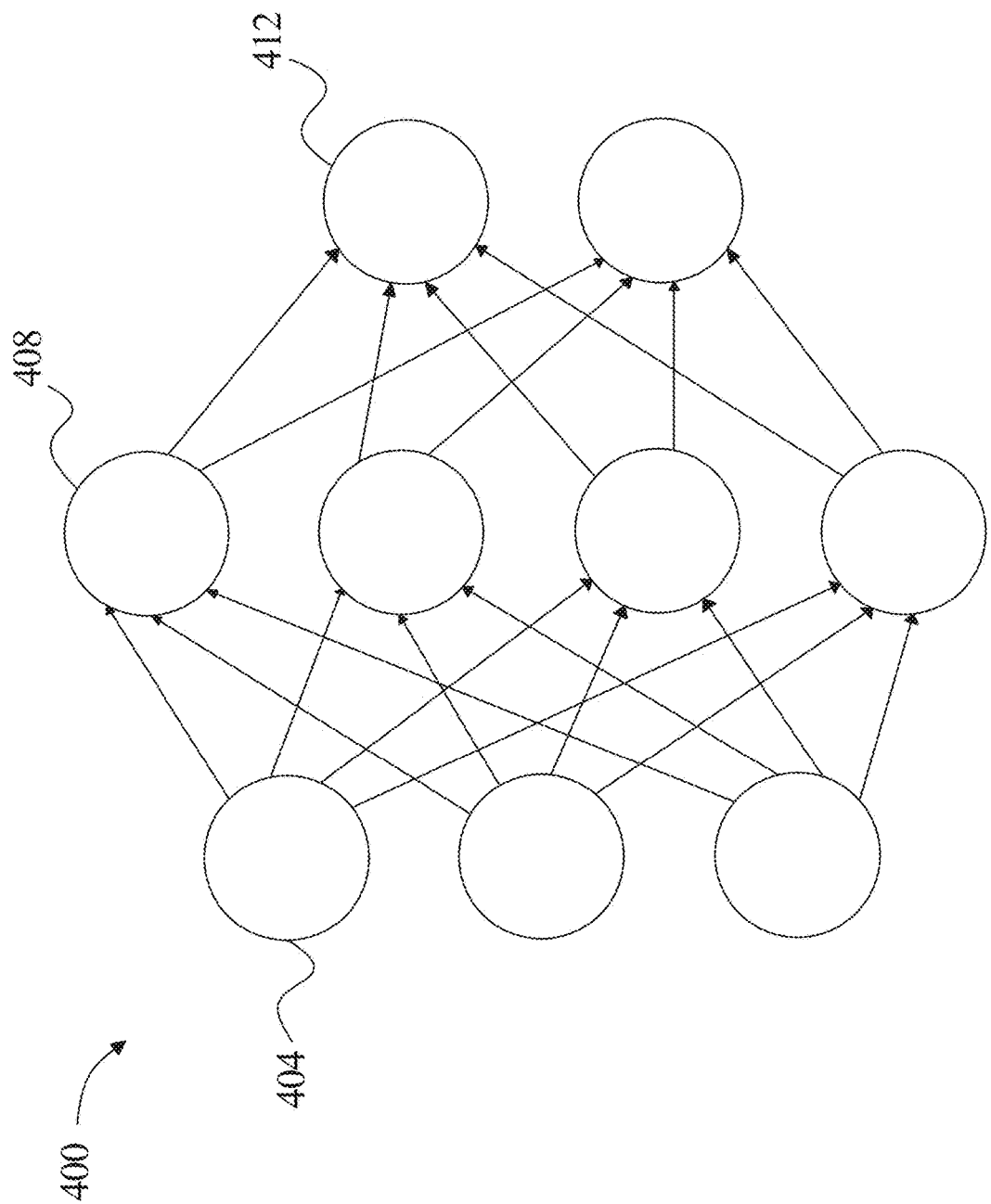
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
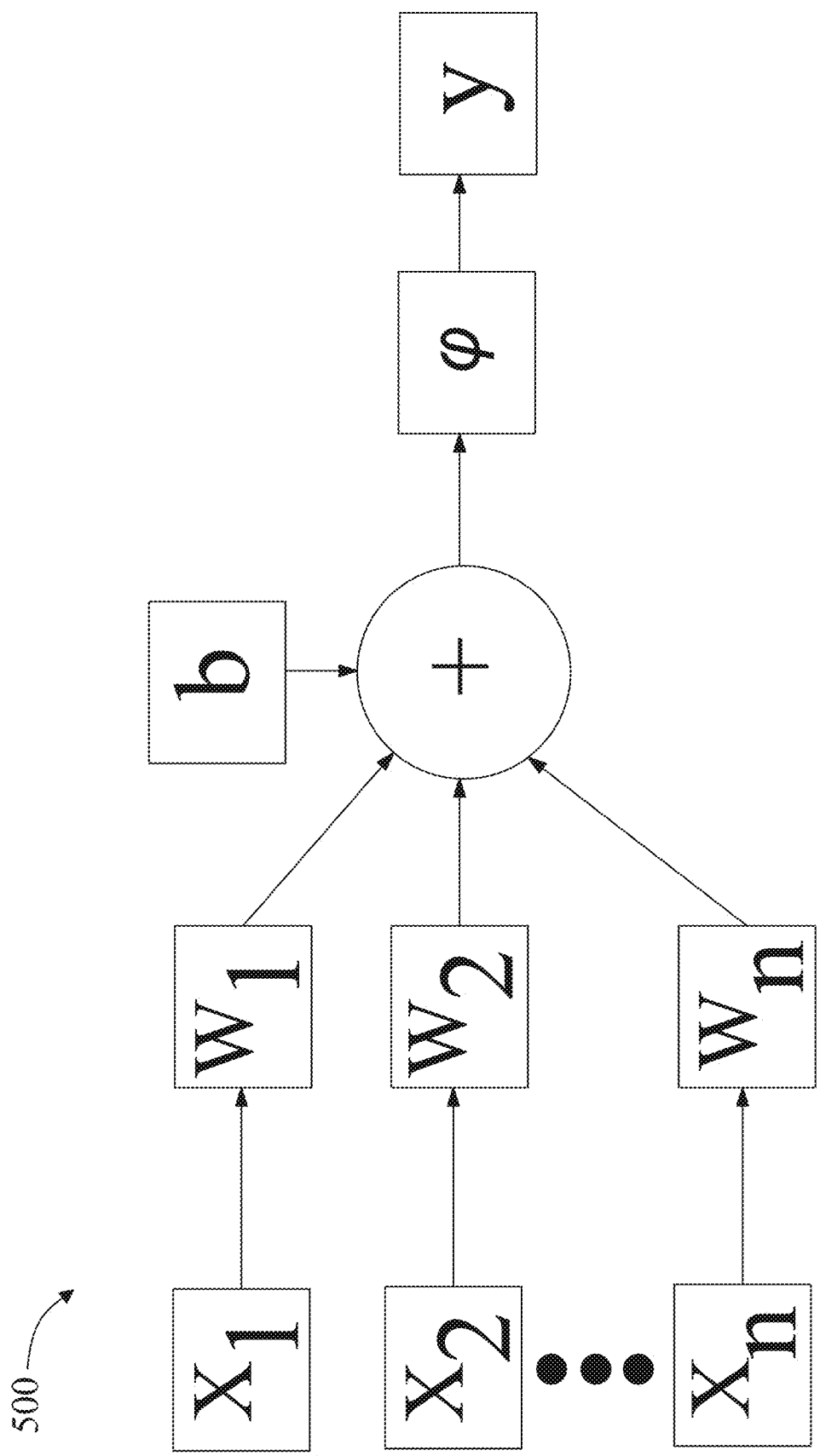
FIG. 5 is a block diagram of an exemplary embodiment of a node.

Referring now to FIG. 5, an exemplary embodiment of a node 500 of a neural network is illustrated. A node may include, without limitation a plurality of inputs x, that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a\,(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
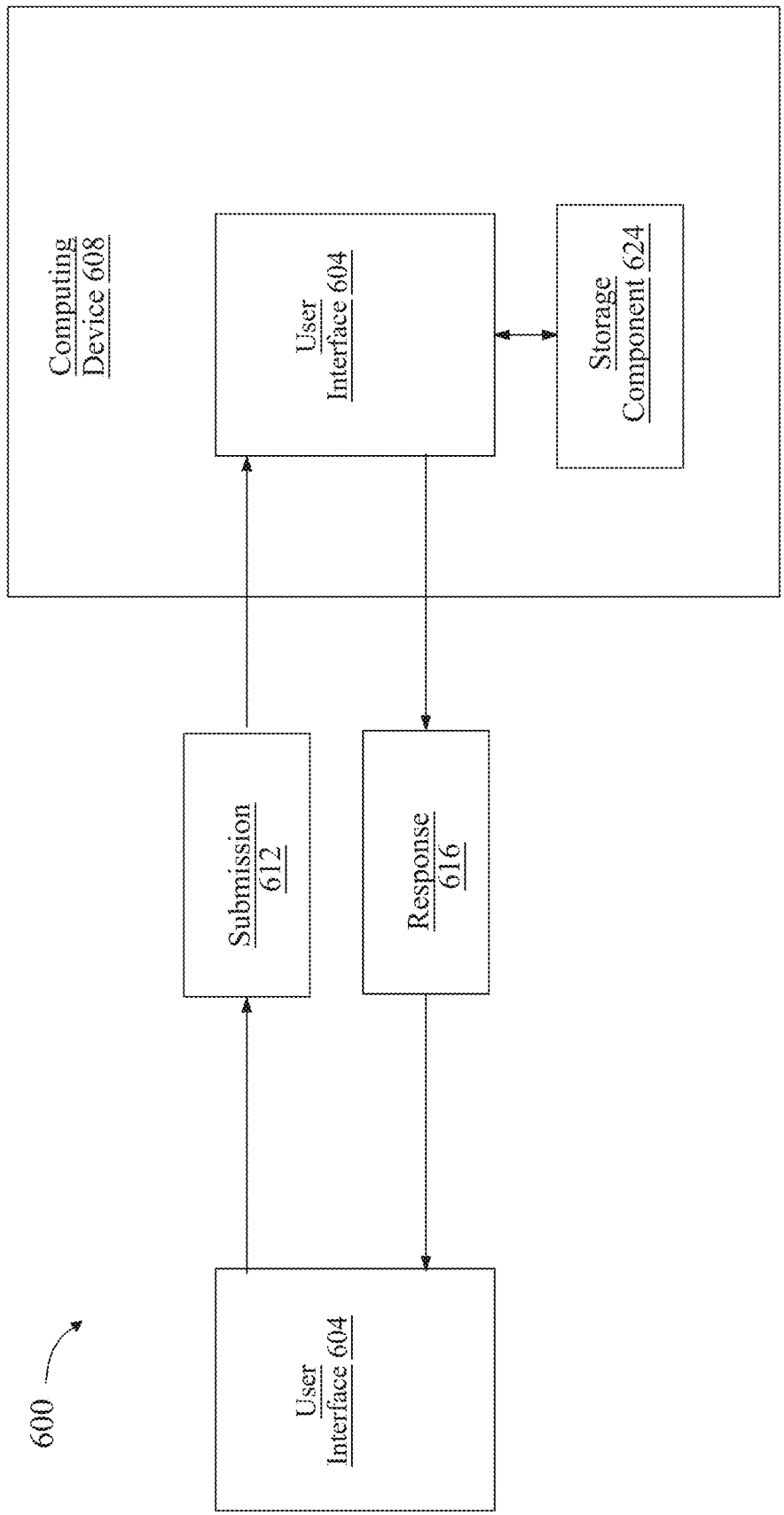
FIG. 6 is a block diagram of a chatbot system.

Referring to FIG. 6, a chatbot system 600 is schematically illustrated. According to some embodiments, a user interface 604 may be communicative with a computing device 608 that is configured to operate a chatbot. In some cases, user interface 604 may be local to computing device 608. Alternatively or additionally, in some cases, user interface 604 may remote to computing device 608 and communicative with the computing device 608, by way of one or more networks, such as without limitation the internet. Alternatively or additionally, user interface 604 may communicate with user device 608 using telephonic devices and networks, such as without limitation fax machines, short message service (SMS), or multimedia message service (MMS). Commonly, user interface 604 communicates with computing device 608 using text-based communication, for example without limitation using a character encoding protocol, such as American Standard for Information Interchange (ASCII). Typically, a user interface 604 conversationally interfaces a chatbot, by way of at least a submission 612, from the user interface 608 to the chatbot, and a response 616, from the chatbot to the user interface 604. In many cases, one or both of submission 612 and response 616 are text-based communication. Alternatively or additionally, in some cases, one or both of submission 612 and response 616 are audio-based communication.

Continuing in reference to FIG. 6, a submission 612 once received by computing device 608 operating a chatbot, may be processed by a processor 620. In some embodiments, processor 620 processes a submission 612 using one or more of keyword recognition, pattern matching, and natural language processing. In some embodiments, processor employs real-time learning with evolutionary algorithms. In some cases, processor 620 may retrieve a pre-prepared response from at least a storage component 624, based upon submission 612. Alternatively or additionally, in some embodiments, processor 620 communicates a response 616 without first receiving a submission 612, thereby initiating conversation. In some cases, processor 620 communicates an inquiry to user interface 604; and the processor is configured to process an answer to the inquiry in a following submission 612 from the user interface 604. In some cases, an answer to an inquiry present within a submission 612 from a user interface 604 may be used by computing device 608 as an input to another function.

Figure 7:
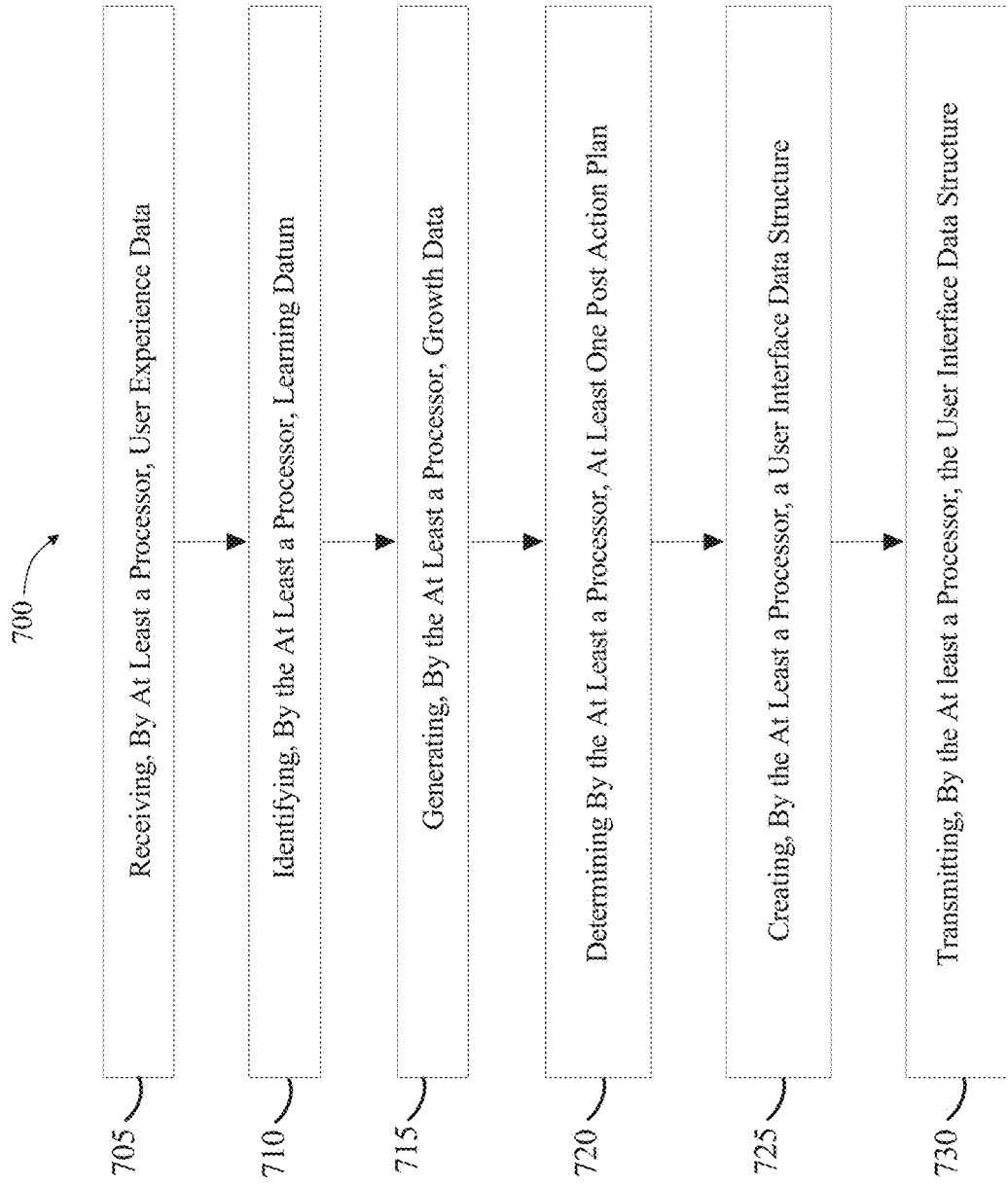
FIG. 7 is a flow diagram illustrating an exemplary embodiment of a method for post action planning.

Referring now to FIG. 7, a method 700 for post action planning is described. At step 705, method 700 includes receiving by at least a processor, user experience data pertaining to a user In some cases, receiving, by the at least a processor, the user experience data further includes receiving user experience data through an input device. In some cases, receiving, by the at least a processor, the user experience data from the input device further includes receiving the user input device through an experience smart assessment. In some cases, input device is configured to receive at least audio-visual data. This step may be implemented as described above with reference to FIGS. 1-7, without limitation.

With continued reference to FIG. 7, at step 705 method 700 includes identifying, by the at least a processor, learning datum as a function of the user experience data. In some cases, identifying, by the at least a processor, the at least a learning datum as a function of the user experience data further includes receiving the at least a learning datum from a user through a learning smart assessment, the learning smart assessment generated as a function of the user experience data. Additionally or alternatively generating learning smart assessment as a function of the user experience data includes generating the learning smart assessment using a machine learning model including receiving assessment training data having a plurality of user experience data correlated to a plurality of smart assessments, training an assessment machine learning model as a function of the assessment training data and generating the learning smart assessment as a function of the assessment machine learning model. In some cases, learning datum includes positive learning datum and negative learning datum. In some cases, identifying, by the at least a processor, the at least a learning datum includes identifying the at least a learning datum using a machine learning model. This step may be implemented as described above with reference to FIGS. 1-7, without limitation.

With continued reference to FIG. 7, at step 710 method 700 includes generating growth data. In some cases, growth data includes a growth score, the growth score configured to contain a numerical score of a user. This step may be implemented as described above with reference to FIGS. 1-7, without limitation.

With continued reference to FIG. 7, at step 715 method 700 includes determining, by the at least a processor, at least one post action plan as a function of the at least a learning datum and the at least a growth data including, receiving post action training data comprising a plurality of the at least a growth data and a plurality of the at least a learning datum correlated to a plurality of post action plans, training a post action machine learning model as a function of the post action training data and generating the post action plan as a function of the post action machine learning model. In some cases, the at least one post action plan contains a plurality of individual action plans, wherein each of the plurality of individual action plans contains a predictive growth score. This step may be implemented as described above with reference to FIGS. 1-7, without limitation.

With continued reference to FIG. 7, at step 720 method 700 includes creating, by the at least a processor, a user interface data structure, wherein the user interface data structure includes the at least one post action plan. This step may be implemented as described above with reference to FIGS. 1-7, without limitation.

With continued reference to FIG. 7, at step 725, method 700 includes transmitting, by the at least a processor, the user interface data structure. In some cases, transmitting, by the at least a processor, the user interface data structure further includes transmitting the user interface data structure to a graphical user interface (GUI) communicatively connected to the at least a processor, wherein the GUI is configured to receive the user interface data structure and display the at least one post action plan as a function of the user interface data structure. In some cases, GUI further includes an interaction component, the interaction component configured to allow a user to select an individual action plan from a plurality of individual action plans in at least one post action plan. This step may be implemented as described above with reference to FIGS. 1-7, without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
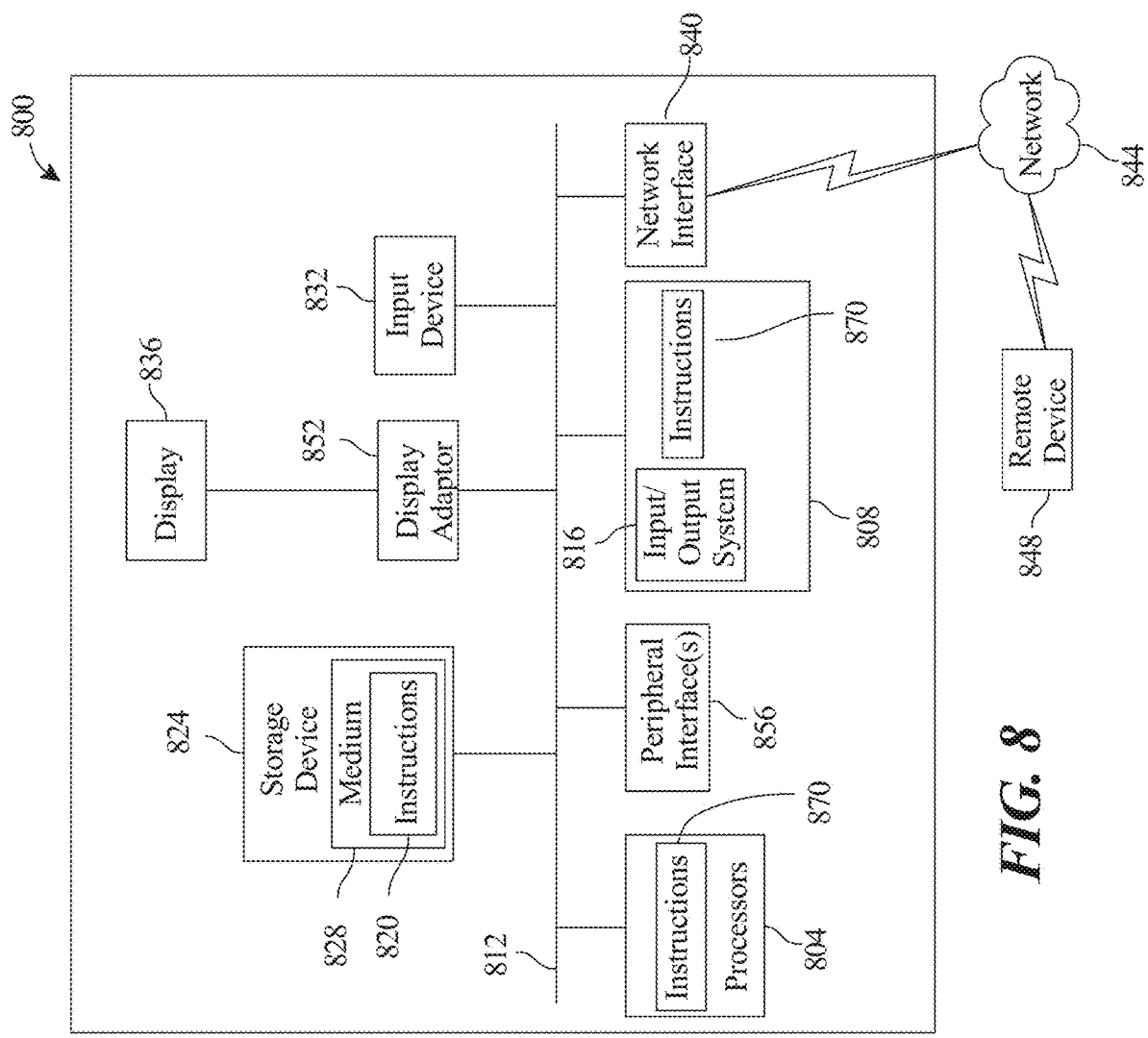
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve apparatuses methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for post action planning, the apparatus comprising:
    at least a processor;
    a memory communicatively connected to the at least a processor, wherein the memory contains instructions configuring the at least a processor to:
        receive user experience data from an input device and a web crawler, wherein the input device comprises an audiovisual input device, wherein the user experience data is further derived from the web crawler, wherein the web crawler is configured to detect at least one data pattern;
        identify at least a learning datum as a function of the user experience datum, wherein identifying the at least a learning datum comprises identifying one or more outcomes associated with the user experience data;
        generate growth data as a function of the user experience data, wherein the growth data includes a growth score generated based on a comparison between the growth data and an optimal output datum describing an optimal response associated with an action from the user experience data, wherein the growth score determines a degree of similarity between the growth data and the optimal output datum;
        determine at least one post action plan as a function of the at least a learning datum and the growth data comprising:
            receiving post action training data comprising a plurality of growth data and a plurality of learning data correlated to a plurality of post action plans;
            training a post action machine learning model as a function of the post action training data, wherein training the post action machine learning model comprises:
                iteratively updating the post action training data as a function of input and output results of the post action machine learning model; and
                retraining the post action machine learning model with an updated post action training data; and
            generating the at least one post action plan as a function of the post action machine learning model;
        create a user interface data structure, wherein the user interface data structure comprises the at least one post action plan; and
        transmit the at least one post action plan and the user interface data structure.

2. The apparatus of claim 1, wherein receiving the user experience data further comprises receiving the user experience data through an experience smart assessment.

3. The apparatus of claim 1, wherein the apparatus further comprises the input device.

4. The apparatus of claim 1, wherein identifying the at least a learning datum as a function of the user experience data further comprises receiving the at least a learning datum from a user through a learning smart assessment, wherein the at least a processor is configured to generate the learning smart assessment a function of the user experience data.

5. The apparatus of clam 4, wherein generating the learning smart assessment as a function of the user experience data comprises generating the learning smart assessment using a machine learning model, wherein generating the learning smart assessment using the machine learning model comprises:
    receiving assessment training data comprising a plurality of user experience data correlated to a plurality of smart assessments;
    training an assessment machine learning model as a function of the assessment training data; and
    generating the learning smart assessment as a function of the assessment machine learning model.

6. The apparatus of claim 1, wherein the at least a learning datum comprises a positive learning datum and negative learning datum.

7. The apparatus of claim 1, wherein identifying the at least a learning datum comprises identifying the at least a learning datum using a machine learning model.

8. The apparatus of claim 1, wherein the growth score comprises a numerical score of a user.

9. The apparatus of claim 1, wherein the at least one post action plan contains a plurality of individual action plans, wherein each of the plurality of individual action plans contains an individual predictive growth score.

10. The apparatus of claim 1, further comprising a graphical user interface (GUI) communicatively connected to the at least a processor, the GUI configured to:
    receive the user interface data structure; and
    display the at least one post action plan as a function of the user interface data structure.

11. A method for post action planning, the method comprising:
- receiving by at least a processor, user experience data pertaining to a user from an input device and a web crawler, wherein the input device comprises an audio-visual input device, wherein the user experience data is further derived from the web crawler, wherein the web crawler is configured to detect at least one data pattern;
- identifying, by the at least a processor, at least a learning datum as a function of the user experience data, wherein identifying the at least a learning datum comprises identifying one or more outcomes associated with the user experience data;
- generating, by the at least a processor, growth data as a function of the user experience data, wherein the growth data includes a growth score generated based on a comparison between the growth data and an optimal output datum describing an optimal response associated with an action from the user experience data, wherein the growth score determines a degree of similarity between the growth data and the optimal output datum;
- determining, by the at least a processor, at least one post action plan as a function of the at least a learning datum and the growth data comprising:
  - receiving post action training data comprising a plurality of growth data and a plurality of learning data correlated to a plurality of post action plans;
  - training a post action machine learning model as a function of the post action training data, wherein training the post action machine learning model comprises:
    - iteratively updating the post action training data as a function of input and output results of the post action machine learning model; and
    - retraining the post action machine learning model with an updated post action training data; and
  - generating the at least one post action plan as a function of the post action machine learning model;
- creating, by the at least a processor, a user interface data structure, wherein the user interface data structure comprises the at least one post action plan; and
- transmitting, by the at least a processor, the at least one post action plan and the user interface data structure.

12. The method of claim 11, wherein the input device is configured to receive at least audio data.

13. The method of claim 11, wherein identifying, by the at least a processor, the at least a learning datum as a function of the user experience data further comprises receiving the at least a learning datum from the user through a learning smart assessment, the learning smart assessment generated, by the at least a processor, as a function of the user experience data.

14. The method of clam 13, wherein generating the learning smart assessment as a function of the user experience data comprises generating the learning smart assessment using a machine learning model comprising, wherein generating the learning smart assessment using the machine learning model comprises:
- receiving assessment training data comprising a plurality of user experience data correlated to a plurality of smart assessments;
- training an assessment machine learning model as a function of the assessment training data; and
- generating the learning smart assessment as a function of the assessment machine learning model.

15. The method of claim 11, wherein the at least a learning datum comprises positive learning datum and negative learning datum.

16. The method of claim 11, wherein identifying, by the at least a processor, the at least a learning datum comprises identifying the at least a learning datum using a machine learning model.

17. The method of claim 11, wherein the growth score comprises a numerical score of the user.

18. The method of claim 11, wherein the at least one post action plan comprises a plurality of individual action plans, wherein each of the plurality of individual action plans comprises a predictive growth score.

19. The method of claim 11, wherein transmitting, by the at least a processor, the user interface data structure further comprises, transmitting, by the at least a processor, the user interface data structure the to a graphical user interface (GUI) communicatively connected to the at least a processor, wherein the GUI is configured to:
- receive the user interface data structure; and
- display the at least one post action plan as a function of the user interface data structure.

* * * * *